(12) United States Patent
O'Heeron et al.

(10) Patent No.: US 6,830,578 B2
(45) Date of Patent: Dec. 14, 2004

(54) TROCAR

(75) Inventors: Peter T. O'Heeron, Houston, TX (US); Patrick C. Newlin, Houston, TX (US)

(73) Assignee: NeoSurg Technologies, Inc., Houston, TX (US)

( * ) Notice: Subject to any disclaimer, the term of this patent is extended or adjusted under 35 U.S.C. 154(b) by 192 days.

(21) Appl. No.: 09/994,321

(22) Filed: Nov. 26, 2001

(65) Prior Publication Data

US 2003/0100914 A1 May 29, 2003

(51) Int. Cl.⁷ ................................................ A61B 17/34
(52) U.S. Cl. .................. 606/185; 606/190; 604/170.01; 604/170.02
(58) Field of Search ................................ 606/185, 190; 604/164.06, 170.01, 164.01, 170.02; 600/129

(56) References Cited

U.S. PATENT DOCUMENTS

| | | | | |
|---|---|---|---|---|
| 5,441,041 A | * | 8/1995 | Sauer et al. ................. 600/106 |
| 5,545,150 A | * | 8/1996 | Danks et al. ................. 604/256 |
| 5,591,192 A | * | 1/1997 | Privitera et al. ............. 606/185 |
| 5,690,663 A | * | 11/1997 | Stephens ..................... 606/185 |
| 5,817,061 A | * | 10/1998 | Goodwin et al. ...... 604/164.03 |
| 6,106,539 A | * | 8/2000 | Fortier ........................ 606/185 |

* cited by examiner

Primary Examiner—Michael H. Thaler
(74) Attorney, Agent, or Firm—Clarence E. Eriksen; Jackson Walker L.L.P.

(57) ABSTRACT

A trocar is disclosed which includes a housing assembly and a cannula assembly attached to the housing assembly to define an axial bore therethrough. The trocar further includes an obturator assembly which slidably engages the axial bore defined by the cannula assembly. The obturator assembly includes a shaft having a piercing end for insertion into a patient and a handling end for gripping by a surgeon. Attached to the piercing end of the shaft is a piercing tip having an upper face and a lower face which taper away from the shaft to form a non-conical, blunt head. The piercing tip further includes wing elements located on opposite sides of the piercing tip between the upper face and lower face. These wing elements have a lateral edges.

5 Claims, 2 Drawing Sheets

TROCAR

BACKGROUND OF THE INVENTION

1. Field of the Invention

The present invention relates to surgical instruments known as trocars which are used in endoscopic surgery to pierce or puncture an anatomical cavity of a patient to provide communication with the cavity during a surgical procedure. More particularly, the present invention relates to an improved non-cutting piercing tip of an obturator assembly of a trocar.

2. Description of the Prior Art

Endoscopic surgery is a significant method of performing surgical operations and has become the surgical procedure of choice due to its patient care advantages over "open surgery." A particular type of endoscopic surgery is laparoscopic surgery. A significant advantage of laparoscopic surgery over open surgery is the decreased post-operative recovery time. In most instances, a patient is able to leave the hospital within hours after laparoscopic surgery has been performed, whereas with open surgery, a patient requires several days of hospital care to recover. Additionally, laparoscopic surgery achieves decreased incidents of post-operative abdominal adhesions, decreased post-operative pain, and enhanced cosmetic results.

Conventionally, a laparoscopic surgical procedure begins with the insufflation of the abdominal cavity with carbon dioxide. The introduction of this gas into the abdominal cavity lifts the abdominal wall away from the internal viscera. The abdominal wall is then pierced or penetrated with a device known as a trocar. A trocar includes a housing assembly, a cannula assembly attached to the housing assembly to form a bore through the trocar, and a piercing element called an obturator. The obturator slides through an access port formed on the upper end of the housing assembly and through the bore of the trocar. After insertion of the trocar through the abdominal wall of the patient, the obturator is removed by the surgeon while leaving the cannula protruding through the abdominal wall. Laparoscopic instruments can then be inserted through the cannula to view internal organs and to perform surgical procedures.

Traditionally, the piercing tip of the obturator of a trocar has employed a sharp cutting blade to assist the surgeon in penetrating the abdominal wall. However, certain trocars, for example, as disclosed in U.S. Pat. No. 5,817,061 to Goodwin, have employed a pair of blunt-edged blades or tissue separators which are located on the tip of the trocar to facilitate the penetration or dissection of tissue.

Both of the trocar assemblies disclosed in U.S. Pat. No. 5,817,061 to Goodwin and U.S. Pat. No. 5,591,192 to Privitera are manufactured and sold by Ethicon Endo-Surgery, Inc. Trocars as described in the '061 and '192 patents have at the time of filing this application been recalled by Ethicon since the tip of the obturator has been prone to failure. In particular, the tip of the trocars disclosed in the '061 and '192 patents have experienced incidents of snapping off during the insertion of the trocar. It is believed that this failure may be attributable to the blunt shape of the tip and the forces to which the tip is subjected upon insertion.

Accordingly, it would be desirable to have an obturator of a trocar with a blunt piercing tip that is structurally capable of resisting increased insertion forces associated with blunt tipped obturators without failing. This novel and useful result has been achieved by the present invention.

SUMMARY OF THE INVENTION

In accordance with the present invention, a trocar is provided which comprises a metal housing assembly and a cannula assembly attached to the housing assembly to define an axial bore therethrough.

A trocar in accordance with the present invention may further comprise an obturator assembly which slidably engages the axial bore defined by the cannula assembly. The obturator assembly comprises a shaft having a piercing end for insertion into a patient and a handling end for gripping by a surgeon. The piercing end of the shaft of the obturator includes a piercing tip having an upper face and a lower face which taper from the shaft to form a non-conical, blunt head. Additionally, wing elements having lateral edges are located on opposite sides of the piercing tip between the upper face and lower face.

In a preferred embodiment of the present invention, the piercing tip of the obturator is removably attached to the shaft of the obturator. Therefore, the obturator may be used with piercing tips of various configurations-such as blunt tips to separate tissue and sharp tips for cutting tissue.

In accordance with the present invention, penetration forces associated with insertion of a blunt tip trocar into a wound track of a patient are reduced due to the improved wing elements. The lateral edges of each wing element widen the wound track to ease insertion of the trocar into the patient. As a result, a trocar in accordance with the present invention is better able to resist these penetration forces without failure as compared to existing blunt tip trocars.

DESCRIPTION OF SPECIFIC EMBODIMENT

Figure 1:
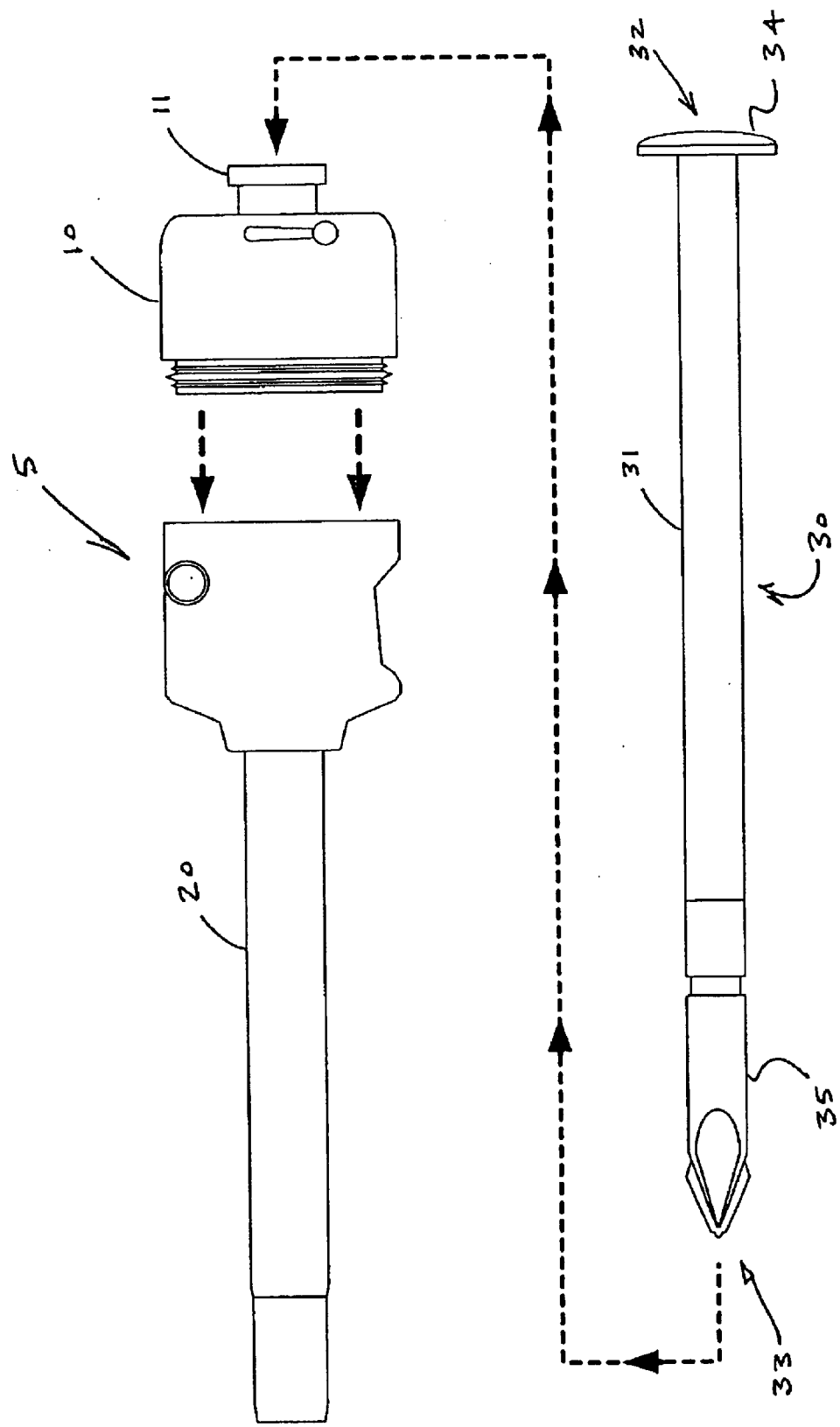
FIG. 1 is an exploded perspective view of an embodiment of a trocar in accordance with the present invention.

With reference to FIG. 1, a trocar 5 in accordance with the present invention comprises a housing assembly 10 to which is attached a cannula assembly 20. The cannula assembly 20 is a hollow tube, and when attached to the housing assembly 10, a bore is defined through the trocar 5.

Still with reference to FIG. 1, a trocar 5 in accordance with the present invention also includes an obturator assembly 30 having a shaft 31 with a handling end 32 and a piercing end 33. An arcuate-shaped cap 34 is attached to the handling end 32 of the shaft 31 to facilitate insertion and manuevering of the obturator assembly 30 by a surgeon. A removable piercing tip 35 is attached to the piercing end 33 of the shaft 31. The obturator assembly 30 slides in the bore that is defined by the combination of housing assembly 10 and cannula assembly 20.

While the shaft 31 of the obturator assembly 30 is preferably formed from a stainless steel material, those skilled in the art will appreciate that the obturator shaft may be formed from a variety of suitable materials.

Figure 2:
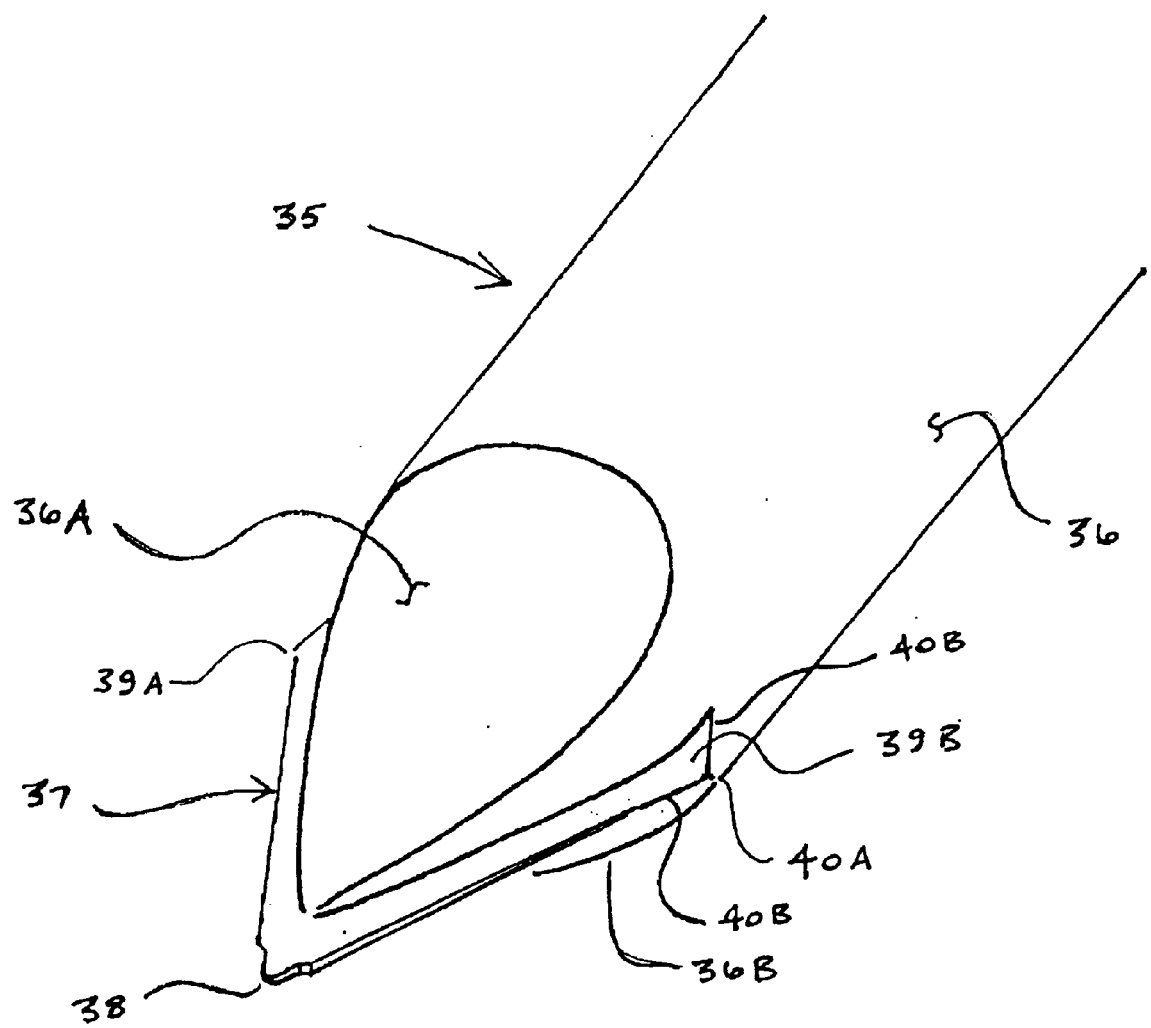
FIG. 2A is an enlarged perspective view of a piercing tip of an obturator in accordance with the present invention.

With reference to FIG. 2, the piercing tip 35 of the obturator assembly 30 is shown in more detail. The piercing tip 35 comprises a body 36 having an upper face 36A and a lower face 36B. The upper face 36A and lower face 36B taper away from the shaft 31. The body 36 of the piercing tip 35 partially houses an insert blade 37. The insert blade 37 comprises a blunt, non-conical head 38 and two wing elements 39A, 39B which protrude outward from the body 36 of the piercing tip 35. Each of the wing elements 39A, 39B come to a point 40A and have lateral edges 40B. The wing elements 39A, 39B are located between the upper face 36A and lower face 36B of the body 36 and are spaced approximately 180 degrees apart. The insert blade 37 may be fabricated from metal or a hard plastic material.

While a preferred embodiment of the present invention includes an insert blade 37 protruding from a body 36 of a piercing tip 35, it is intended that the insert blade and the body of the piercing tip can be fabricated as a monolithic piece from metal or hard plastic.

With respect to FIGS. 1 and 2, in accordance with the present invention, the piercing tip 35 of the obturator assembly 30 is preferably removably attached to the piercing end 33 of the shaft 31 of the obturator. This removability allows a surgeon to interchange between various piercing tips which are tailored to a particular application—such as sharp piercing tips for cutting tissue or blunt piercing tips for separating tissue. The techniques for making removable tips for trocars is well-known in the art, for example as shown in U.S. Pat. No. 5,697,947 to Wolf, which is incorporated herein by reference.

While the piercing tip 35 is preferably removably attached to the piercing end 33 of the shaft 31 of the obturator assembly 30, the piercing tip may also be formed on the piercing end of the shaft such that the obturator assembly is a monolithic piece.

With a trocar in accordance with the present invention, it is believed that less force will be required to insert the obturator assembly into a patient than the force required with conventional trocars. Furthermore, the blunt head of the piercing tip-as opposed to a sharp, conical head—prevents internal structures from being cut if encountered during insertion of the obturator assembly. Still furthermore, the design of the tip of the trocar as illustrated in FIG. 2, forces the penetration forces to act away from the tip, which eases the penetration of the trocar into the patient.

The foregoing and other advantages of the invention will be apparent to those skilled in the art.

What is claimed is:

1. A trocar, comprising:
   (a.) a housing assembly;
   (b.) a cannula assembly attached to the housing assembly and defining an axial bore therethrough; and
   (c.) an obturator assembly for sliding engagement through the axial bore defined by the cannula assembly, said obturator assembly comprising a shaft having a piercing end for insertion into a patient and a piercing tip removably connected to the piercing end of the shaft, said piercing tip comprising:
   (i.) a body having an upper face and a lower face tapering away from the shaft; and
   (ii.) an insert blade residing partially within the body of the piercing tip and protruding outward away from the body of the piercing tip, said insert blade comprising a non-conical, blunt head and two wing elements having lateral edges located 180 degrees apart between the upper face and lower face of the body.

2. The trocar of claim 1, wherein the insert blade is fabricated from metal.

3. The trocar of claim 1, wherein the insert blade is fabricated from plastic.

4. The trocar of claim 1, wherein said shaft further comprises a handling end for gripping.

5. The trocar of claim 4, further comprising an arcuate-shaped cap attached to the handling end of the shaft.

\* \* \* \* \*